United States Patent [19]
Bailey et al.

[11] Patent Number: 4,925,857
[45] Date of Patent: May 15, 1990

[54] PYRIDINYL-1H-PYRAZOLE-1-ALKANA-MIDES AS ANTIARRHYTHMIC AGENTS

[75] Inventors: Denis M. Bailey, East Greenbush; Thomas E. D'Ambra, North Greenbush; Alan M. Ezrin, Colonie, all of N.Y.

[73] Assignee: Sterling Drug Inc., New York, N.Y.

[21] Appl. No.: 327,219

[22] Filed: Mar. 22, 1989

[51] Int. Cl.$^5$ .................. C07D 401/04; A61K 31/415
[52] U.S. Cl. ..................................... 514/341; 514/333; 514/212; 514/318; 546/256; 546/279; 546/193; 546/194; 540/484
[58] Field of Search ............... 546/256, 279, 193, 194; 540/484; 514/333, 341, 212, 318

[56] References Cited

U.S. PATENT DOCUMENTS

| | | | |
|---|---|---|---|
| 4,072,498 | 2/1978 | Moon et al. | 71/92 |
| 4,182,895 | 1/1980 | Bailey | 548/378 |
| 4,695,566 | 9/1987 | Heinemann et al. | 514/234 |

FOREIGN PATENT DOCUMENTS 299407 1/1989 European Pat. Off. .

OTHER PUBLICATIONS

Ezrin et al. *FASEB Journal* 2, A1557 (1988).

*Primary Examiner*—Jane T. Fan
*Attorney, Agent, or Firm*—Philip E. Hansen; Paul E. Dupont

[57] ABSTRACT

N-[(alkylamino)alkyl]-4,5-diaryl-1H-pyrazole-1-acetamides, wherein at least one of the aryl substituents is a pyridine, useful for treating cardiac arrhythmias in mammals, are prepared by reacting a lower-alkyl ester of pyrazole-1-acetic acid with an appropriate diamine.

15 Claims, No Drawings

PYRIDINYL-1H-PYRAZOLE-1-ALKANAMIDES AS ANTIARRHYTHMIC AGENTS

BACKGROUND OF THE INVENTION

1. Field of the Invention

The present invention relates to novel N-[(alkylamino)alkyl]-4,5-diaryl-1H-pyrazole-1-acetamides, wherein at least one of the aryl substituents is a pyridine, processes for the synthesis of said pyrazole-1-acetamides, and methods for treating cardiac arrhythmia in mammals utilizing said pyrazole-1-acetamides.

2. Information Disclosure Statement

U.S. Pat. No. 4,695,566 to Heinemann et al. discloses as antiarrythmic agents 1H-pyrazol-3-yl(and 1H-pyrazol-5-yl)oxyacetamides of general formula

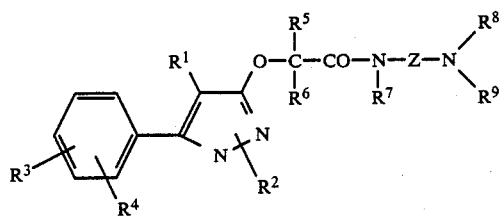

Specifically disclosed are (1) N-[2-(diethylamino)ethyl]-2-[(5-phenyl-1H-pyrazol-3-yl)oxy]acetamide, example 5, and (2) N-[3-(diethylamino)propyl]-2-[(5-phenyl-1H-pyrazol-3-yl)oxy]acetamide, example 24.

U.S. Pat. No. 4,182,895 to Bailey discloses as an intermediate in the synthesis of 1-amino-lower-alkyl-3,4-diphenyl-1H-pyrazoles "β-[1-(3,4-diphenyl-1H-pyrazolyl)]-N,N-dimethylpropionamide" at column 8, line 63 to 64.

U.S. Pat. No. 4,072,498 to Moon and Kornis discloses N,N,α,α-tetramethyl-3,4-diphenylpyrazole-1-acetamide (example 160) and N,N,α-trimethyl-5-(2-thienyl)-pyrazole-1-acetamide (example 29) as herbicides.

Ezrin et al. [FASEB Journal 2, A1557(1988)] describes the antiarrhythmic activity of N-[3-(diethylamino)propyl]-4,5-diphenyl-1H-pyrzole-1-acetamide fumarate.

European patent application 299,407, published Jan. 18, 1989 discloses a series of 4,5-diaryl-1H-pyrazole-1-alkanamides as aantiarrhythmic agents.

SUMMARY OF THE INVENTION

In a product aspect the invention relates to compounds of the formula I

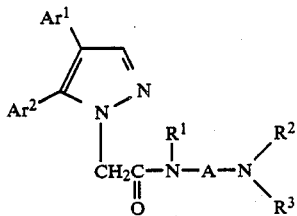

or acid-addition salt thereof wherein $R^1$ is hydrogen or lower-alkyl; $R^2$ and $R^3$ are independently hydrogen, lower-alkyl, or hydroxy lower-alkyl, or $R^2$ and $R^3$ together form a straight or branched alkylene chain of four to six carbons; A is $CH_2CH(OH)CH_2$ or $(CH_2)_n$ wherein n is an integer from two to eight; $Ar^1$ and $Ar^2$ are independently pyridinyl, phenyl, or phenyl substituted with methoxy, hydroxy or halogen; and at least one of $Ar^1$ and $Ar^2$ is pyridinyl.

Lower-alkyl as used herein describes linear or branched hydrocarbon chains of four or fewer carbon atoms; lower-alkoxy as used herein describes linear or branched alkyloxy substituents containing four or fewer carbon atoms; halogen describes bromine, chlorine or fluorine.

In a further product aspect, the invention relates to compositions for treating cardiac arrhythmia which comprise compounds of the formula I together with pharmaceutically acceptable excipients or diluents as required.

In a process aspect, the invention relates to a method for treating cardiac arrhythmia in a mammal which comprises administering to said mammal an antiarrhythmically effective amount of a compound of formula I.

Processes for preparing a compound of formula I comprise reacting a pyrazole-1-acetate with an amine.

DETAILED DESCRIPTION INCLUSIVE OF PREFERRED EMBODIMENTS

The synthesis of compounds of the invention may be outlined as shown in scheme A wherein $R^4$ is lower-alkyl.

SCHEME A

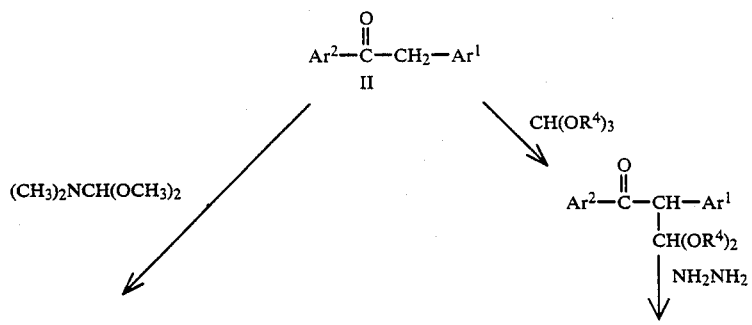

SCHEME A -continued

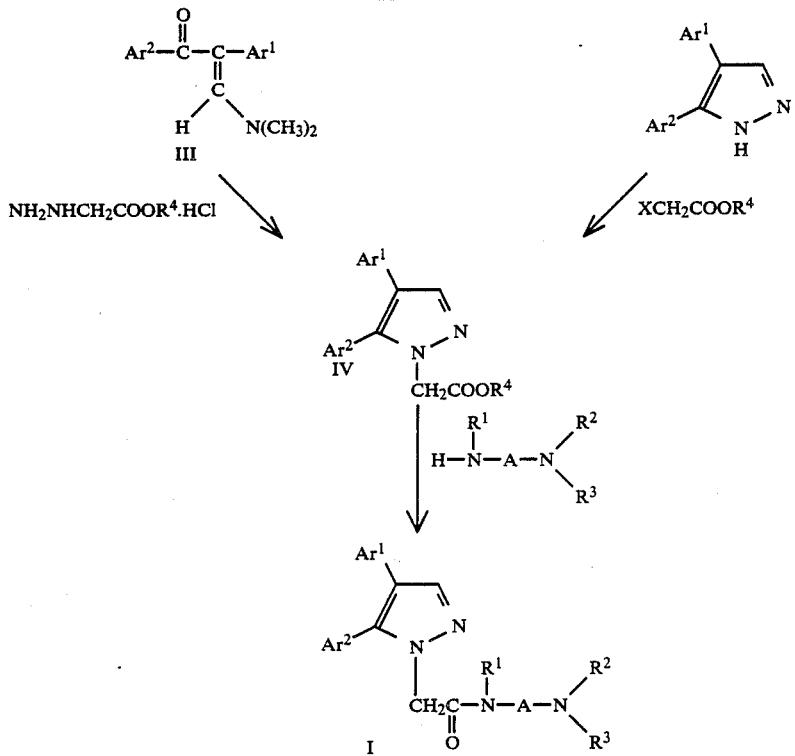

An appropriately substituted diarylethanone (II) is reacted with an excess, preferably about 10% excess, of dimethylformamide dimethylacetal in an inert solvent, preferably methyl t-butyl ether, at 20° to 100° C., preferably 53°-56° C. The diaryl ethanone may be synthesized by the procedure of Nahm and Weinreb (Tet. Lett. 1981, 3815-3818) from the appropriate acid and the appropriate hetaryllithium or hetarylmethyl lithium species via the N-methoxy-N-methyl amide of said acid.

The $\beta$-ketoenamine (III) resulting from the reaction of diarylethanone and DMF acetal is reacted with the salt of a lower-alkyl hydrazinoacetate, preferably ethyl hydrazinoacetate hydrochloride in a suitable solvent, preferably ethanol, at 20°-100° C., preferably 40°-50° C., to yield substantially pure 4,5-diaryl-1H-pyrazole-1-acetate of formula IV.

Alternatively, in those cases where the diarylethanone appears to exist primarily as its enol tautomer, the diarylethanone is reacted with an orthoformate ester and a Lewis acid, preferably ethyl orthoformate and boron trifluoride etherate, in an inert solvent, preferably methylene chloride, at −78° to 0° C. to form a 3,3-dialkoxy-1-propanone. The propanone is reacted with hydrazine at 0° to 100° C., preferably at about 78° C., in a suitable solvent, preferably ethanol, to provide a 3,4-(4,5-)diaryl-1H-pyrazole. The pyrazole is converted to the pyrazole-1-acetate by alkylation with an α-haloacetate ester (X is Cl or Br), preferably ethyl chloroacetate, using a base, preferably sodium hydride, in an inert solvent, preferably DMF, at 0° to 100° C., preferably at room temperature.

The lower-alkyl ester, preferably a methyl or ethyl ester, of the suitably substituted 4,5-diarylpyrazole-1-alkanoic acid (IV) is reacted with an excess of a primary or secondary amine of formula III at 20° to 150° C., preferably at 90° to 100° C. When the amine is valuable, the ester IV is preferably reacted with about one equivalent of the amine V in the presence of a tertiary amine, preferably diisopropylethylamine, optionally in an inert solvent.

The compounds of formula I are useful both in the free base form and the form of acid-addition salt, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts that is, salts whose anions are relatively innocuous to the animal organism in medicinal doses of the salts so that the beneficial properties inherent in the free base are not vitiated by side effects ascribable to the anions. In practicing the present invention it is convenient to form the hydrochloride, fumarate, toluenesulfonate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet, and nuclear magnetic resonance, spectroscopy. The course of the reactions and the identity and homogeneity of the products were assessed by thin layer chromatography (TLC) or gas-liquid chromatography (GLC). The starting materials are either commercially available or may be prepared by procedures well known in the art.

In the following procedures melting points are given in degrees C and are uncorrected. The abbreviation THF stands for tetrahydrofuran, DMF stands for N,N-dimethylformamide and Ac stands for the acetyl residue, $CH_3CO$.

GENERAL PROCEDURE 1

N-methoxy-N-methylamides

To solution of 1 equivalent of the appropriate acid chloride in methylene chloride was added 1.2 equivalents of solid methoxymethylamine hydrochloride. 2.5 equivalents of triethylamine was added at about 0° C. and the reaction was stirred at room temperature for 48 hours. The triethylamine hydrochloride was filtered off, the methylene chloride solution was washed with water, dried and stripped to yield the amide as an oil.

By this procedure were made (1) N-methoxy-N-methyl-3-pyridinecarboxamide, (2) N-methoxy-N-methylbenzenacetamide, (3) N-methoxy-N-methylbenzamide and (4) N-methoxy-N-methyl-2-pyridinecarboxamide.

GENERAL PROCEDURE 2

Desoxybenzoin Analogs

A solution of 1.2 equivalents of the appropriate picoline or bromopyridine in ether at −78° C. under nitrogen was treated with 1 equivalent of N-butyllithium in hexane and then stirred one hour without cooling to generate the anion. The reaction was again cooled to −78° C. and an ether solution containing 1 equivalent of the appropriate N-methoxy-N-methylamide from procedure 1 was added dropwise. After the addition was complete the reaction was allowed to come to room temperature and stirred for 3 hr. Any excess butyllithium was quenched with isopropyl alcohol at −78° C., water was added at room temperature, and the ether was stripped off. The product was treated with excess 0.25M NaOH, extracted into methylene chloride, and stripped.

By this procedure were obtained (1) 1,2-bis(2-pyridinyl)ethanone, (2) 1-(3-pyridinyl)-2-(2-pyridinyl)ethanone, (3) 2-phenyl-1-(3-pyridinyl)ethanone, (4) 1-phenyl-2-(2-pyridinyl)ethanone.

EXAMPLE 1

Ethyl-5-phenyl-4-(2-pyridinyl)-1H-pyrazole-1-acetate

A solution of 26 g (0.132 mol) of 1-phenyl-2-(2-pyridinyl)ethanone and 19.3 mL (0.145 mol) of dimethylformamide dimethylacetal in 100 mL of methyl t-butyl ether was refluxed 4 hr. Because TLC on silica gel with 10% isopropylamine in ethyl acetate showed little reaction, another 20 mL of DMF dimethylacetal was added and the solution refluxed a further 6 hr. The solvent was stripped and the resulting crude, oily β-ketoenamine was dissolved in 400 mL of ethanol. The ethanol solution was heated to 40° with 22 g (0.143 mol) of ethyl hydrazinoacetate hydrochloride for about 1.5 hr. The solvent was stripped, and the resulting impure product was dissolved in a small amount of methylene dichloride and applied to a column of 850 g of silica gel. The column was eluted with 2:1 hexane-ethyl acetate to yield 25 g of yellow solid product, mp 98°–100° C. after evaporation of the solvent.

EXAMPLE 2

Ethyl 4-phenyl-5-(3-pyridinyl)-1H-pyrazole-1-acetate

By a process substantially similar to that of example 1, 23 g of ethyl 4-phenyl-5-(3-pyridinyl)-1H-pyrazole-1-acetate, mp 90°–91° C. from cyclohexane, was obtained from 29 g (0.147 mol) of 2-phenyl-1-(3-pyridinyl)ethanone, 21.5 mL (0.162 mol) of DMF dimethylacetal and 20.6 g (0.133 mol) of ethyl hydrazinoacetate hydrochloride.

EXAMPLE 3

Ethyl 4-(2-pyridinyl)-5-(3-pyridinyl)-1H-pyrazole-1-acetate

By a process substantially similar to that of example 1, 9 g of ethyl 4-(2-pyridinyl)-5-(3-pyridinyl)-1H-pyrazole-1-acetate, mp 43°–46° C., was obtained from 11.0 g (0.055 mol) of 1-(3-pyridinyl)-2-(2-pyridinyl)ethanone, 8.1 mL (0.061 mol) of DMF dimethylacetal and 9.8 g (0.064 mol) of ethyl hydrazinoacetate hydrochloride. The chromatographic purification utilizes 3:1 hexane-acetone in place of the 2:1 hexane-ethyl acetate of example 1.

EXAMPLE 4

Ethyl 4,5-bis(2-pyridinyl)-1H-pyrazole-1-acetate

A solution of 15 mL (0.089 mol) of triethyl orthoformate in 100 mL of methylene chloride was stirred under nitrogen at −78° C. and 13.2 mL (0.108 mol) of boron trifluoride etherate was added. The solution was allowed to warm to 0° C., recooled to −78° C., and a solution of 8.0 g (0.04 mol) of 1.2-bis(2-pyridinyl)ethanone in 75 mL of methylene chloride was added, followed after 30 min by 22 mL (0.132 mol) of diisopropylethylamine in 30 mL of methylene chloride. The reaction was stirred 45 min at −78° C., poured into 400 mL of water containing 10 g of $NaHCO_3$ and stirred 20 min. The phases were separated, the methylene chloride layer was dried over $MgSO_4$ and stripped to yield about 17 g of crude 3,3-diethoxy-1,2-bis(2-pyridinyl)-1-propanone.

The propanone was dissolved in 1 L of ethanol, 5.8 mL (0.12 mol) of hydrazine hydrate was added, and the mixture was heated to reflux for 1 hr. The ethanol was stripped off in vacuo, and the residue was put through a 600 g silica gel column eluting with 1:1 hexane-acetone to yield about 4 g of 4,5-bis(2-pyridinyl)-1H-pyrazole as a light tan solid after removal of solvent.

The 4 g of pyrazole was added to a suspension of 0.52 g (21.6 mmol) of sodium hydride (0.86 g of a 60% dispersion in oil) in 50 mL of DMF. The mixture was stirred 15 minutes and 2.3 mL (21.6 mmol) of ethyl chloroacetate was added. After 30 minutes water was added cautiously to destroy any excess sodium hydride. The solvent was removed in vacuo, the residue was partitioned between ethyl acetate and water, and the organic layer was dried and stripped to a yellow oil. The oil was dissolved in 1:1 acetone-hexane and filtered through silica gel to yield 4 g of ethyl 4,5-bis(2-pyridinyl)-1H-pyrazole-1-acetate as an oil containing about 5% of an impurity.

EXAMPLE 5

N-[3-(Diethylamino)propyl]-5-phenyl-4-(2-pyridinyl)-1H-pyrazole-1-acetamide

A solution of 10 g (0.032 mol) of ethyl 5-phenyl-4-(2-pyridinyl)pyrazole-1-acetate of example 1 in 15 mL (0.095 mol) of 3-(diethylamino)propanamine was heated at 100° for 3 hr. The excess amine was stripped in vacuo and the residue distributed between water and ether. The ether solution was dried over MgSO$_4$, stripped and applied to 350 g of silica gel in a small amount of methylene chloride. The column was eluted with 20:1 acetone-triethylamine and a light yellow oil was obtained that crystallized upon triturating with cyclohexane to yield 5.4 g of product, mp 82°–83° C.

EXAMPLE 6

N-[3-(Diethylamino)propyl]-4-phenyl-5-(3-pyridinyl)-1H-pyrazole-1-acetamide hemihydrate By procedure substantially similar to that of example 5, 6.7 g of N-[3-(diethylamino)propyl]-4-phenyl-5-(3-pyridinyl)-1H-pyrazole-1-acetamide hemihydrate, mp 61°–62° C. was obtained from 10 g (0.032 mol) of ethyl 4-phenyl-5-(3-pyridinyl)-1H-pyrazole-1-acetate of example 2 and 15 mL (0.096 mol) of 3-(diethylamino)propanamine.

EXAMPLE 7

N-[3-(Diethylamino)propyl]-4-(2-pyridinyl)-5-(3-pyridinyl)-1H-pyrazole-1-acetamide dihydrochloride By a process substantially similar to that of example 5, 2.9 g of N-[3-(diethylamino)propyl]-4-(2-pyridinyl)-5-(3-pyridinyl)-1H-pyrazole-1-acetamide dihydrochloride was obtained from 2 g (6.5 mmol) of ethyl 4-(2-pyridinyl)-5-(3-pyridinyl)-1H-pyrazole-1-acetate of example 3 and 3.1 mL (19.5 mmol) of 3-(diethylamino)propanamine. The free base was converted to the dihydrochloride by dissolving in ethanol, adding excess HCl in ether, and recrystallizing the resulting solid from ethanol-ether to yield 2.6 g of product, mp 149°–150° C.

EXAMPLE 8

N-[3-(Diethylamino)propyl]-4,5-bis(2-pyridinyl)-1H-pyrazole-1-acetamide

By a process substantially similar to that of example 5 it is contemplated that N-[3-(diethylamino)propyl]-4,5-bis(2-pyridinyl)-1H-pyrazole-1-acetamide may be synthesized from ethyl bis(2-pyridinyl)-1H-pyrazole-1-acetate of example 4 and 3-(diethylamino)propanamine.

EXAMPLE 9

N-[3-(Diethylamino)propyl]-5-(3-methoxyphenyl)-N-methyl-4-(4-pyridinyl)-1-acetamide By a process substantially similar to that of example 5, it is contemplated that N-[3-(diethylamino)propyl]-5-(3-methoxyphenyl)-N-methyl-4-(4-pyridinyl)-1H-pyrazole-1-acetamide may be synthesized from ethyl 5-(3-methoxyphenyl)-4-(4-pyridinyl)-1H-pyrazole-1-acetate and N-methyl-N',N'-diethyl-1,3-propanediamine. It is anticipated that the desired ester may be synthesized from 4-picoline and m-anisoyl chloride by the methods of procedures 1 and 2, followed by a process substantially similar to example 1.

EXAMPLE 10

N-[3-Diethylamino)-2-hydroxypropyl]-4-(4-fluorophenyl)-5-(4-pyridinyl)-1H-pyrazole-1-acetamide By a process substantially similar to that of example 5, it is contemplated that N-[3-(diethylamino)-2-hydroxypropyl]-4-(4-fluorophenyl)-5-(4-pyridinyl)-1H-pyrazole-1-acetamide may be synthesized from ethyl 4-(4-fluorophenyl)-5-(4-pyridinyl)-1H-pyrazole-1-acetate and 1-amino-3-(diethylamino)-2-propanol. It is anticipated that the desired ester may be synthesized from 1-(4-pyridinyl)-2-(4-fluorophenyl)ethanone [Lantos et al. *J. Org. Chem.* 53, 4223–4227 (1988)] by a process substantially similar to that of example 1 or example 4.

Other embodiments of the invention may be synthesized from the appropriate 4,5-diaryl-1H-pyrazole-1-acetates. The starting materials for compounds of the invention having varying $R^1$, $R^2$ and $R^3$ are described in U.S. Pat. No. 4,870,095. U.S. application D.N. 7398C of Denis Bailey has now issued to U.S. Pat. No. 4,870,095. which is incorporated herein by reference.

The antiarrhythmic activity of compounds of the invention was demonstrated by the following procedure.

Duncan Hartley guinea pigs (600–900 grams) of either sex were anesthetized with urethane (1.4 g/kg, i.p.) and supplemented as needed. An intravenous route for drug administration was established using microbore tubing inserted into the jugular vein. The induction of arrhythmias by aconitine hydrochloride (34 g/kg) was evaluated in control guinea pigs given 1 cc saline as an intravenous bolus 10 minutes prior to aconitine challenge.

Compounds to be tested were administered intravenously 10 minutes prior to aconitine challenge at an initial dosage of 30 mg/kg. This dosage was reduced in subsequent animals if severe cardiac rhythm disturbances persisted beyond two minutes after injection in the first guinea pig tested. All drugs were tested at the maximally tolerated dose (identified by the lack of arrhythmias in the EKG prior to aconitine challenge). Compounds were administered in saline as 1 cc bolus injections (n=5-9).

Time intervals between aconitine injection and the appearance of arrhythmias were determined. Specifically noted was the time until the onset of (i) the first premature ventricular contraction (PVC); (ii) the first sustained run of ventricular tachycardia consisting of 10 or more ventricular beats (VTACH); and (iii) the time until the appearance of ventricular fibrillation lasting longer than 15 seconds (VFIB). The average time and standard error of the mean until the appearance of these arrhythmias were calculated for each treatment group and compared to concurrent controls using a one-way analysis of variance. Activity was defined as a statistically significant delay in the onset of PVC, VTACH and VFIB time course compared to control values.

The following table summarizes the results obtained from the testing of representative compounds of the invention.

| Example | Minutes to | | |
| No. | PVC | VTACH | VFIB |
| Control | 1.0–1.2 | 1.0–2.0 | 4.0–6.0 |

-continued

| Example No. | Minutes to | | |
|---|---|---|---|
| | PVC | VTACH | VFIB |
| 5 | 18.9 | 23.2 | 44.9 |
| 6 | 7.6 | 16.2 | 19.9 |
| 7 | 10.2 | 60.0 | 60.0 |

The compounds of the invention can be prepared for use by conventional pharmaceutical procedures: that is, by dissolving or suspending them or their pharmacuetically acceptable salts in a pharmaceutically acceptable vehicle, e.g., water, aqueous alcohol, glycol, oil solution or oil-water emulsion, for parenteral or oral administration; by incorporating them in unit dosage form as capsules or tablets for oral administration either alone or in combination with conventional adjuvants or excipients, e.g., calcium carbonate, starch, lactose, talc, magnesium stearate, gum acacia, and the like.

The percentage of active component in the composition and method for treating or preventing arrhythmia can be varied so that a suitable dosage is obtained. The dosage administered to a particular patient is variable depending upon the clinician's judgement using as the criteria: the route of administration, the duration of treatment, the size and condition of the patient, the potency of the active component, and the patient's response thereto. An effective dosage amount of active component can thus be determined by the clinician considering all criteria and utilizing his best judgement on the patient's behalf.

We claim:

1. A compound of formula

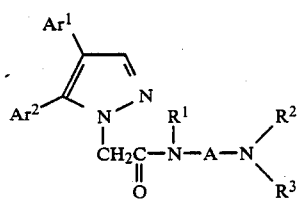

or acid-addition salt thereof wherein $R^1$ is hydrogen or lower-alkyl; $R^2$ and $R^3$ are independently hydrogen, lower-alkyl, or hydroxy lower-alkyl; or $R^2$ and $R^3$ together form a straight or branches alkylene chain of four to six carbons; A is $CH_2CH(OH)CH_2$ or $(CH_2)_n$ wherein n is an integer from two to eight; $Ar^1$ and $Ar^2$ are independently pyridinyl, phenyl, or phenyl substituted with methoxy, hydroxy or halogen; and at least one of $Ar^1$ and $Ar^2$ is pyridinyl.

2. A compound according to claim 1 wherein $Ar^1$ and $Ar^2$ are independently pyridinyl or phenyl.

3. A compound according to claim 2 wherein $R^1$ is hydrogen.

4. A compound according to claim 3 wherein A is $(CH_2)_3$.

5. N,N-[3-Diethylamino)propyl]-5-phenyl-4-(2-pyridinyl)-1H-pyrazole-1-acetamide or an acid addition salt or solvate thereof according to claim 4.

6. N,N-[3-(Diethylamino)propyl]-4-phenyl-5-(3-pyridinyl)-1H-pyrazole-1-acetamide or an acid addition salt or solvate thereof according to claim 4.

7. N-[3-(Diethylamino)propyl]-4-(2-pyridinyl)-5-(3-pyridinyl)-1H-pyrazole-1-acetamide according to claim 4.

8. A composition for treating cardiac arrhythmias comprising an amount of a compound according to claim 1 effective to treat cardiac arrhythmias together with one or more pharmaceutically acceptable excipients or diluents.

9. A composition for treating cardiac arrhythmias comprising an amount of a compound according to claim 3 effective to treat cardiac arrhythmias together with one or more pharmaceutically acceptable excipients or diluents.

10. A composition for treating cardiac arrhythmias comprising an amount of a compound according to claim 4 effective to treat cardiac arrhythmias together with one or more pharmaceutically acceptable excipients or diluents.

11. A composition for treating cardiac arrhythmias comprising an amount of N-[3-(diethylamino)propyl]-5-phenyl-4-(2-pyridinyl)-1H-pyrazole-1-acetamide or pharmaceutically acceptable acid addition salt thereof according to claim 5 effective to treat cardiac arrhythmias together with one or more pharmaceutically acceptable excipients or diluents.

12. A method for treating cardiac arrhythmias in a susceptible subject which comprises the step of administering an amount of a compound according to claim 1 effective to treat cardiac arrhythmias.

13. A method for treating cardiac arrhythmias in a susceptible subject which comprises the step of administering an amount of a compound according to claim 3 effective to treat cardiac arrhythmias.

14. A method for treating cardiac arrhythmias in a susceptible subject which comprises the step of administering an amount of a compound according to to claim 4 effective to treat cardiac arrhythmias.

15. A method for treating cardiac arrhythmias in a susceptible subject which comprises the step of administering an amount of N-[3-(diethylamino)propyl]-5-phenyl-4-(2-pyridinyl)-1H-pyrazole-1-acetamide or pharmaceutically acceptable acid addition salt thereof according to claim 5 effective to treat cardiac arrhythmias.

* * * * *